US012588802B2

(12) United States Patent
Ono

(10) Patent No.: US 12,588,802 B2
(45) Date of Patent: Mar. 31, 2026

(54) CONNECTION JOINT, ENDOSCOPE, AND METHOD OF CONNECTING TUBE AND CONNECTION JOINT

(71) Applicant: OLYMPUS CORPORATION, Tokyo (JP)

(72) Inventor: Kazuki Ono, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 679 days.

(21) Appl. No.: 17/897,478

(22) Filed: Aug. 29, 2022

(65) Prior Publication Data

US 2022/0409023 A1      Dec. 29, 2022

Related U.S. Application Data

(63) Continuation of application No. PCT/JP2020/009535, filed on Mar. 5, 2020.

(51) Int. Cl.
*A61B 1/00*       (2006.01)
*A61B 1/015*      (2006.01)
*A61B 1/018*      (2006.01)

(52) U.S. Cl.
CPC .......... *A61B 1/00128* (2013.01); *A61B 1/015* (2013.01)

(58) Field of Classification Search
CPC ..... A61B 1/00128; A61B 1/015; A61B 1/018; A61B 1/00119
See application file for complete search history.

(56) References Cited

U.S. PATENT DOCUMENTS

| | | | | |
|---|---|---|---|---|
| 5,735,793 A | * | 4/1998 | Takahashi .......... | A61B 1/00128 600/153 |
| 5,800,398 A | * | 9/1998 | Hahnle .............. | A61B 17/3417 604/164.11 |
| 2001/0025135 A1 | | 9/2001 | Naito et al. | |
| 2019/0246885 A1 | * | 8/2019 | Karikomi .............. | A61B 1/015 |

FOREIGN PATENT DOCUMENTS

| | | |
|---|---|---|
| JP | H10-108830 A | 4/1998 |
| JP | 2001-245842 A | 9/2001 |
| JP | 2001-252243 A | 9/2001 |
| JP | 2001-258832 A | 9/2001 |
| JP | 2012-223214 A | 11/2012 |

OTHER PUBLICATIONS

International Search Report dated May 12, 2020 received in PCT/JP2020/009535.

* cited by examiner

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

A connection joint includes: a first sleeve that is formed such that an end portion of a first tube arranged in an endoscope is externally fitted to the first sleeve; a first pusher configured to apply bias to the first sleeve from an outer peripheral side of the first sleeve; and a first bias releasing portion configured to press the first pusher in an outer peripheral direction of the first sleeve to release the bias.

15 Claims, 9 Drawing Sheets

FIG.10

CONNECTION JOINT, ENDOSCOPE, AND METHOD OF CONNECTING TUBE AND CONNECTION JOINT

CROSS-REFERENCE TO RELATED APPLICATION

This application is a continuation of International Application No. PCT/JP2020/009535, filed on Mar. 5, 2020, the entire contents of which are incorporated herein by reference.

BACKGROUND

1. Technical Field

The present disclosure relates to a connection joint, an endoscope, and a method of connecting a tube and a connection joint.

2. Related Art

In the related art, an endoscope is configured to insert an insertion portion into a subject, such as a patient, and acquire, by an imaging apparatus, image data inside the subject and perform treatment using a treatment tool or the like. The endoscope includes a water supply path for washing and cleaning dirt from an observation window of the imaging apparatus, an air supply path for injecting air to the inside of an organ to easily observe an observation region of the subject, and the like, and the paths are configured with tubes made of PTFE or the like.

If the channel is configured with a single long tube, operability at the time of assembly or maintenance of the endoscope is reduced; therefore, an endoscope in which a channel is configured by connecting a plurality of tubes by a connection sleeve has been proposed (for example, see Japanese Laid-open Patent Publication No. 2001-258832).

SUMMARY

In some embodiments, a connection joint includes: a first sleeve that is formed such that an end portion of a first tube arranged in an endoscope is externally fitted to the first sleeve; a first pusher configured to apply bias to the first sleeve from an outer peripheral side of the first sleeve; and a first bias releasing portion configured to press the first pusher in an outer peripheral direction of the first sleeve to release the bias.

In some embodiments, an endoscope includes: a tube; and a case in which a sleeve to which the tube is externally fitted and an elastic material that presses the tube toward the sleeve are integrated.

In some embodiments, provided is a method of connecting a tube to a connection joint, the tube constituting a conduit path arranged inside an insertion portion of an endoscope. The method includes: releasing bias by pressing a pusher, which is applying the bias to a sleeve from an outer peripheral side of the sleeve, in an outer peripheral direction of the sleeve by a bias releasing portion; fitting an end portion of the tube to the sleeve for which contact with the pusher is being released; releasing pressing of the pusher by moving the bias releasing portion in a first direction such that the pusher moves in a direction away from an outer peripheral surface of the sleeve; and pressing the pusher toward the outer peripheral surface of the sleeve by moving the bias releasing portion in a second direction.

In some embodiments, provided is a method of connecting a tube and a connection joint, the tube being arranged in an endoscope. The method includes: pressing a pusher, which is applying bias to a sleeve from an outer peripheral side of the sleeve, toward the outer peripheral side of the sleeve to separate the sleeve from the pusher; fitting a tube to the sleeve externally; releasing pressing to the pusher; and applying, by the pusher, bias to an outer peripheral surface of the tube.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 10 is a cross-sectional view of a connection joint according to a third embodiment of the disclosure.

DETAILED DESCRIPTION

Figure 1:
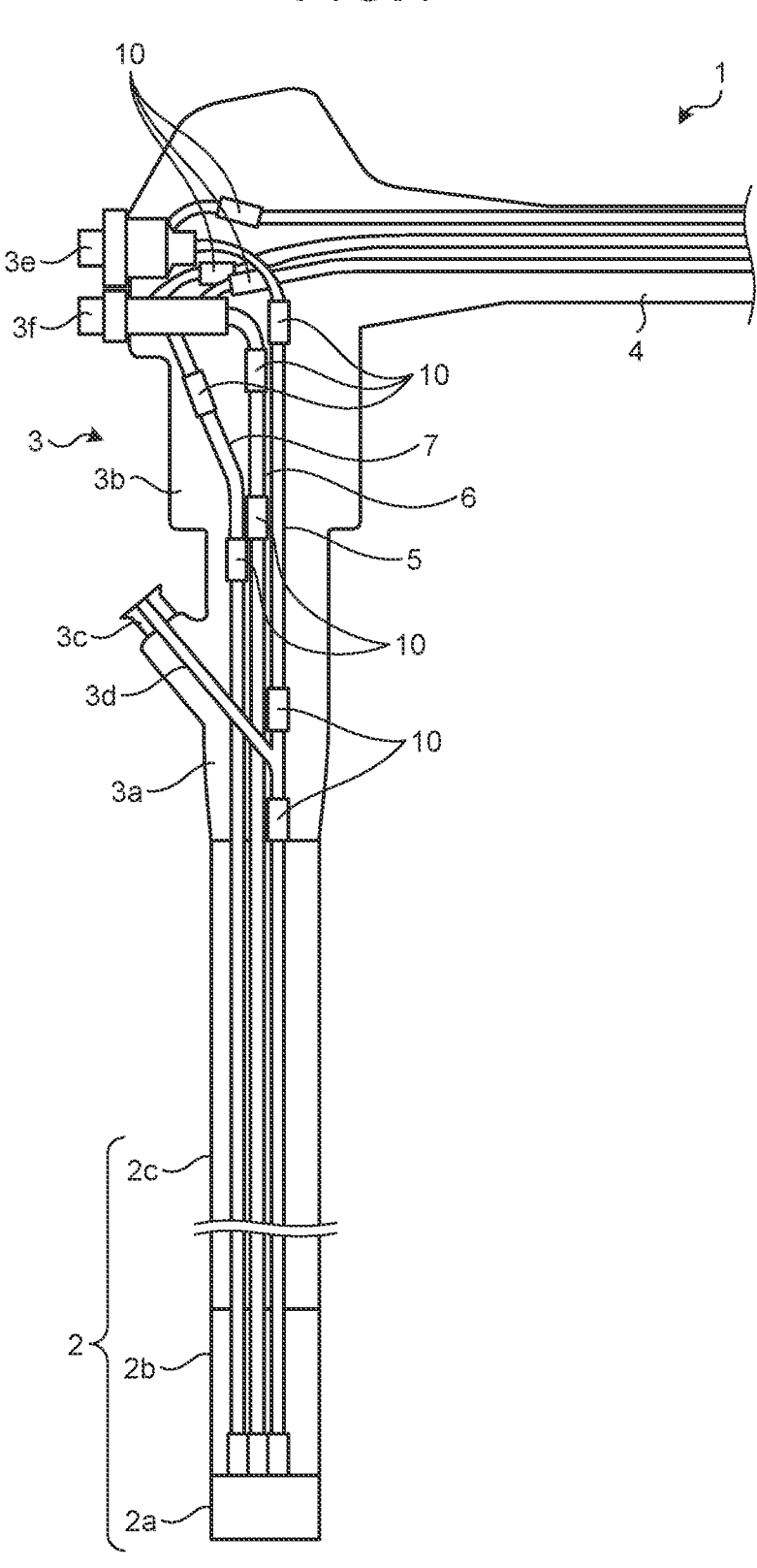
FIG. 1 is a schematic diagram of an endoscope according to a first embodiment of the disclosure.

As modes (hereinafter, embodiments) for carrying out the present disclosure, an endoscope in which a tube that constitutes a conduit path is connected by a connection joint and which is arranged in an insertion portion will be described below. Further, the present disclosure is not limited to the embodiments below. Furthermore, in each of the drawings referred to in the following description, shapes, sizes, and positional relationships are only schematically illustrated so that the content of the present disclosure may be understood. In other words, the present disclosure is not limited to only the shapes, the sizes, and the positional relationships illustrated in the drawings. Moreover, the drawings may include portions that have different dimensions or ratios.

First Embodiment

FIG. 1 is a schematic diagram of an endoscope 1 according to a first embodiment of the disclosure. As illustrated in FIG. 1, the endoscope 1 according to the first embodiment includes an insertion portion 2 that is inserted into a subject, an operating unit 3 that is located at a side of a proximal end portion of the insertion portion 2 and that is grasped by an operator, and a flexible universal cord 4 that is extended from the operating unit 3.

The insertion portion 2 is implemented by a light guide cable, an electrical cable, an optical fiber, various kinds of channels, and the like. The insertion portion 2 includes a distal end portion 2a that includes an observation unit, an illumination unit, and openings for various kinds of channels, a bending portion 2b that is formed of a plurality of bending pieces and that is freely bendable, and a flexible tube portion 2c that is arranged at a side of a proximal end portion of the bending portion 2b and that has flexibility. In the distal end portion 2a, an opening portion for arranging: the light guide cable for illuminating inside of the subject; an imaging unit that captures an image of the inside of the subject; and a treatment tool path is arranged.

The operating unit 3 includes a main body 3a and a gripper unit 3b that is grasped by an operator who operates the endoscope 1. In the main body 3a, a treatment tool insertion portion 3c for inserting a treatment tool, such as a biopsy, forceps or a laser scalpel, into a body cavity of the subject is arranged. A proximal end portion of a treatment tool path 3d is connected to the treatment tool insertion portion 3c. The treatment tool path 3d is arranged from the distal end portion 2a over the flexible tube portion 2c. The treatment tool, such as a biopsy forceps, is inserted from the treatment tool insertion portion 3c to the treatment tool path 3d, and pushed toward the opening of the distal end portion 2a.

A bending operation unit (not illustrated) for operating bending portion 2b is arranged in the gripper unit 3b. Further, in the gripper unit 3b, a suction switch 3e for a suction path 11 and an air supply/water supply switch 3f for an air supply path 12 and a water supply path 13 are arranged. The suction path 11, the air supply path 12, and the water supply path 13 are arranged from the distal end portion 2a over the flexible tube portion 2c. The treatment tool path 3d, a suction path 5, an air supply path 6, and a water supply path 7 connect tubes 40 by connection joints 10.

Figure 2:
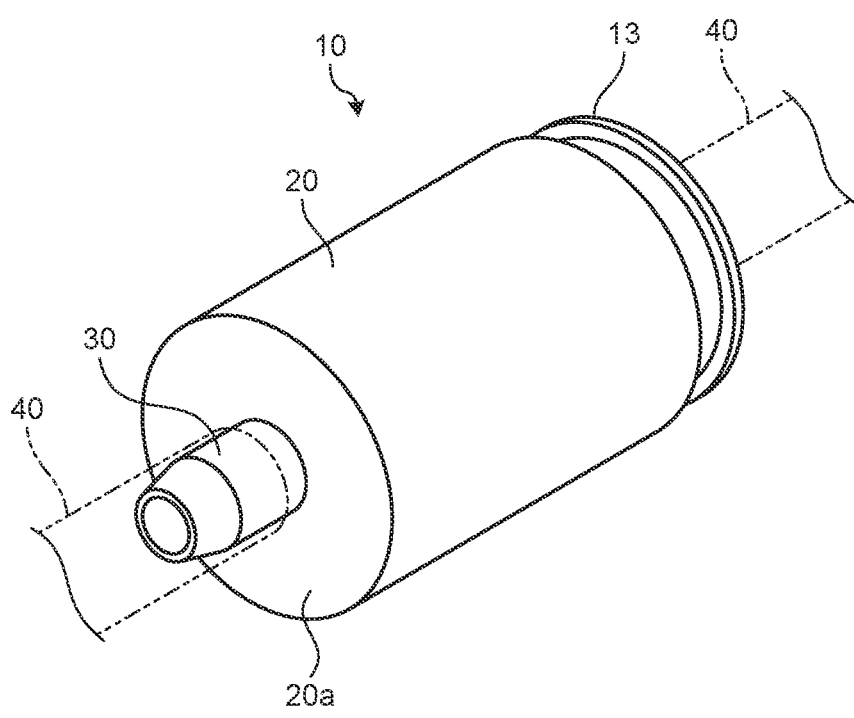
FIG. 2 is a perspective view of a connection joint that is used in the endoscope according to the first embodiment of the disclosure.
Figure 3:
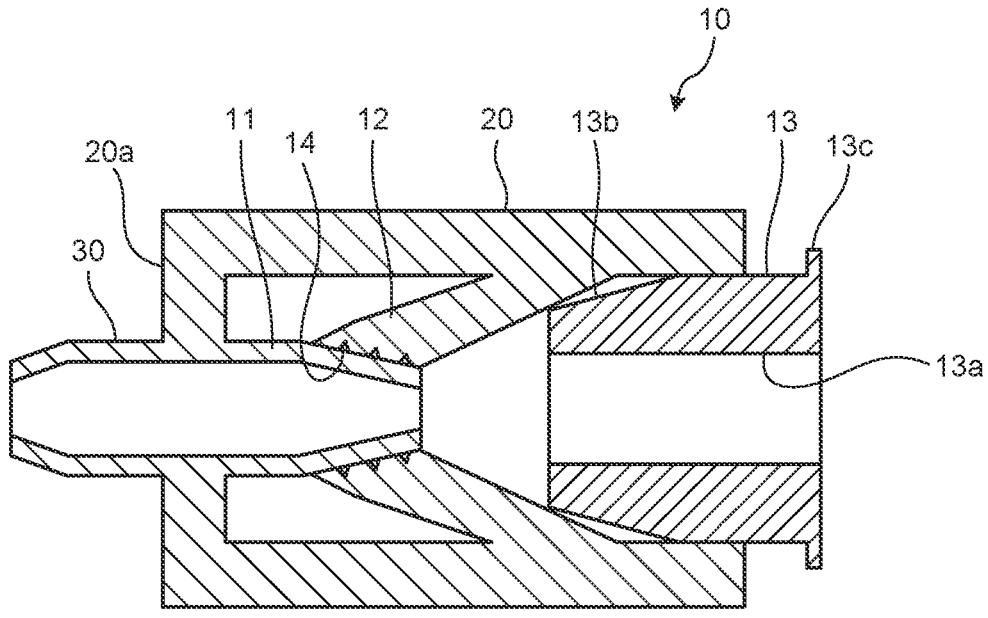
FIG. 3 is a cross-sectional view of the connection joint in an axial direction in FIG. 2.

A connection joint used in the endoscope 1 will be described in detail below. FIG. 2 is a perspective view of the connection joint 10 used in the endoscope 1 according to the first embodiment of the disclosure. FIG. 3 is a cross-sectional view of the connection joint 10 in an axial direction in FIG. 2.

The connection joint 10 includes a sleeve 11 that is fitted to an end portion of the water supply tube, a pusher 12 that applies bias to the sleeve 11 from an outer peripheral side, and a bias releasing portion 13 that releases the bias applied by the pusher 12. The sleeve 11 has a certain shape in which an end portion has a tapered shape such that fitting of an end portion of the water supply tube 40 (see FIG. 4A and FIG. 4B) can be easily performed. The sleeve 11 is held inside a cylindrical case main body 20 that has a bottomed surface 20a, and a connection portion 30 that constitutes the water supply path together with the sleeve 11 and the water supply tube is arranged on the bottomed surface 20a of the case main body 20. The end portion of the water supply tube 40 that is incorporated in the universal cord 4 from the operating unit 3 is fitted to the connection portion 30, and the water supply tube 40 is fixed to the connection portion 30 by an adhesive or the like if needed. The connection portion 30 also has a tapered shape such that the tube 40 can be easily inserted and removed, similarly to the sleeve 11.

Figure 4A:
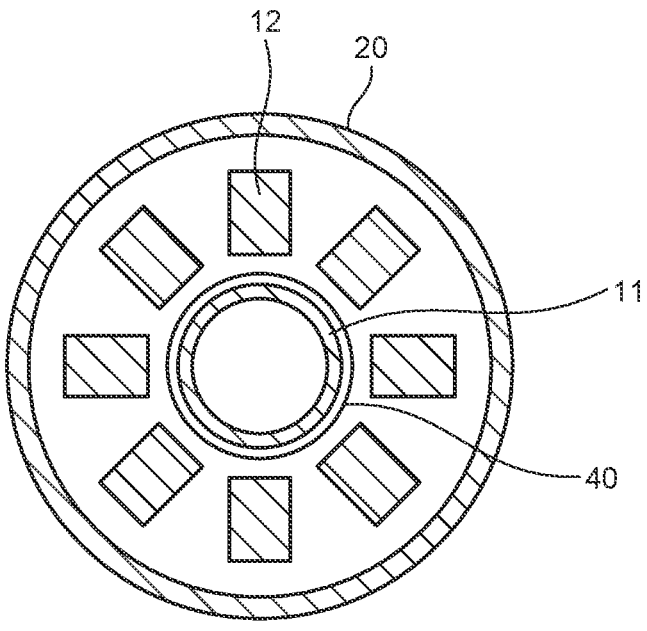
FIG. 4A is a cross-sectional view in a direction perpendicular to the axial direction for explaining a configuration of the connection joint.
Figure 4B:
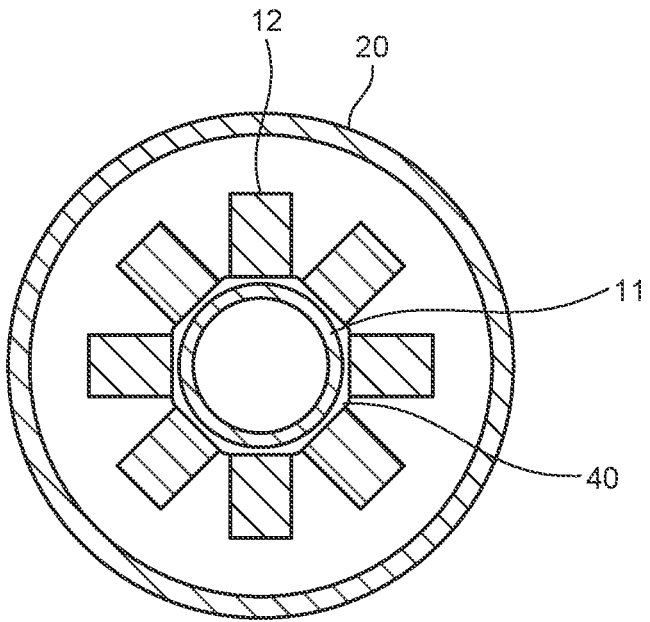
FIG. 4B is a cross-sectional view in the direction perpendicular to the axial direction for explaining a configuration of the connection joint.

FIG. 4A and FIG. 4B are cross-sectional views in a direction perpendicular to the axial direction for explaining a configuration of the connection joint 10. As illustrated in FIG. 4A and FIG. 4B, the pusher 12 includes eight plate springs, biases the sleeve 11 from an outer peripheral side of the sleeve 11 when the bias releasing portion 13 is not pushed into the case main body 20 (FIG. 4B), and fixes the water supply tube 40 that is fitted to an outer peripheral portion of the sleeve 11. In a state in which the bias releasing portion 13 is pushed into the case main body 20 (FIG. 4A), the plate springs included in the pusher 12 are pressed to the outer peripheral side of the sleeve 11 by a distal end portion 13b of the bias releasing portion 13 (to be described later), so that the contact with the sleeve 11 (the sleeve 11 fitted to the water supply tube 40) is released. The number of the plate springs included in the pusher 12 is not limited to eight, but it is preferable to increase a contact area with the water supply tube 40 to make it easy to perform pressing and fixing together with the sleeve 11.

A plurality of grooves 14 that are dug in a direction that is not parallel to a longitudinal axis direction are formed on a surface of the pusher 12 that comes into contact with the sleeve 11, and function as a retainer for preventing coming off of the water supply tube 40.

A through hole 13a for inserting the water supply tube 40 is formed inside the bias releasing portion 13, and the bias releasing portion 13 has a cylindrical shape having an outer diameter that is slightly smaller than an inner diameter of the case main body 20. Further, the distal end portion 13b of the bias releasing portion 13 has a tapered shape such that the bias releasing portion 13 can be easily pushed into the case main body 20. A flange portion 13c for inserting and removing the bias releasing portion 13 to and from the case main body 20 is formed on a proximal end side of the bias releasing portion 13.

Figure 5:
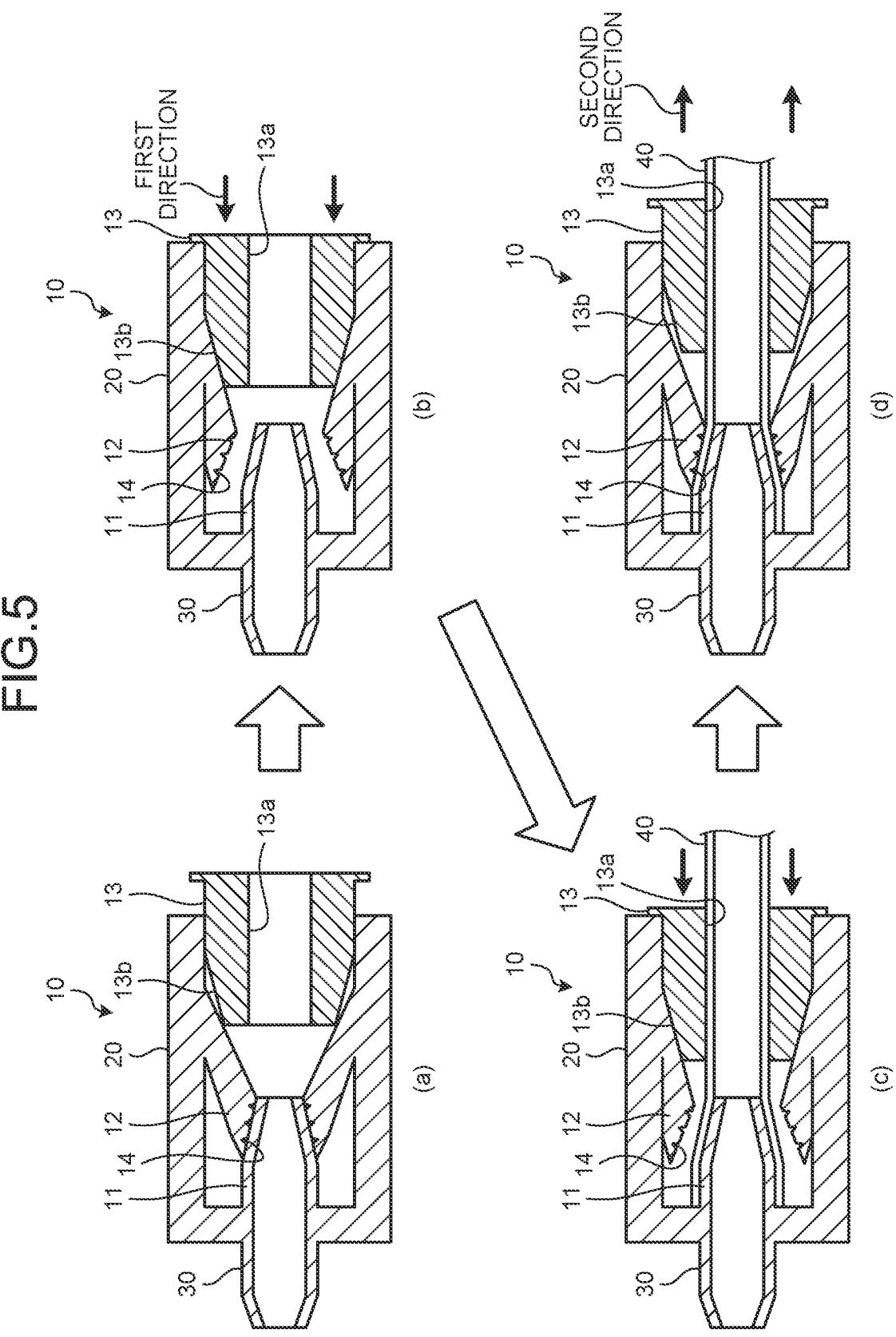
FIG. 5 is a diagram for explaining connection between a water supply tube and the connection joint.
Figure 6:
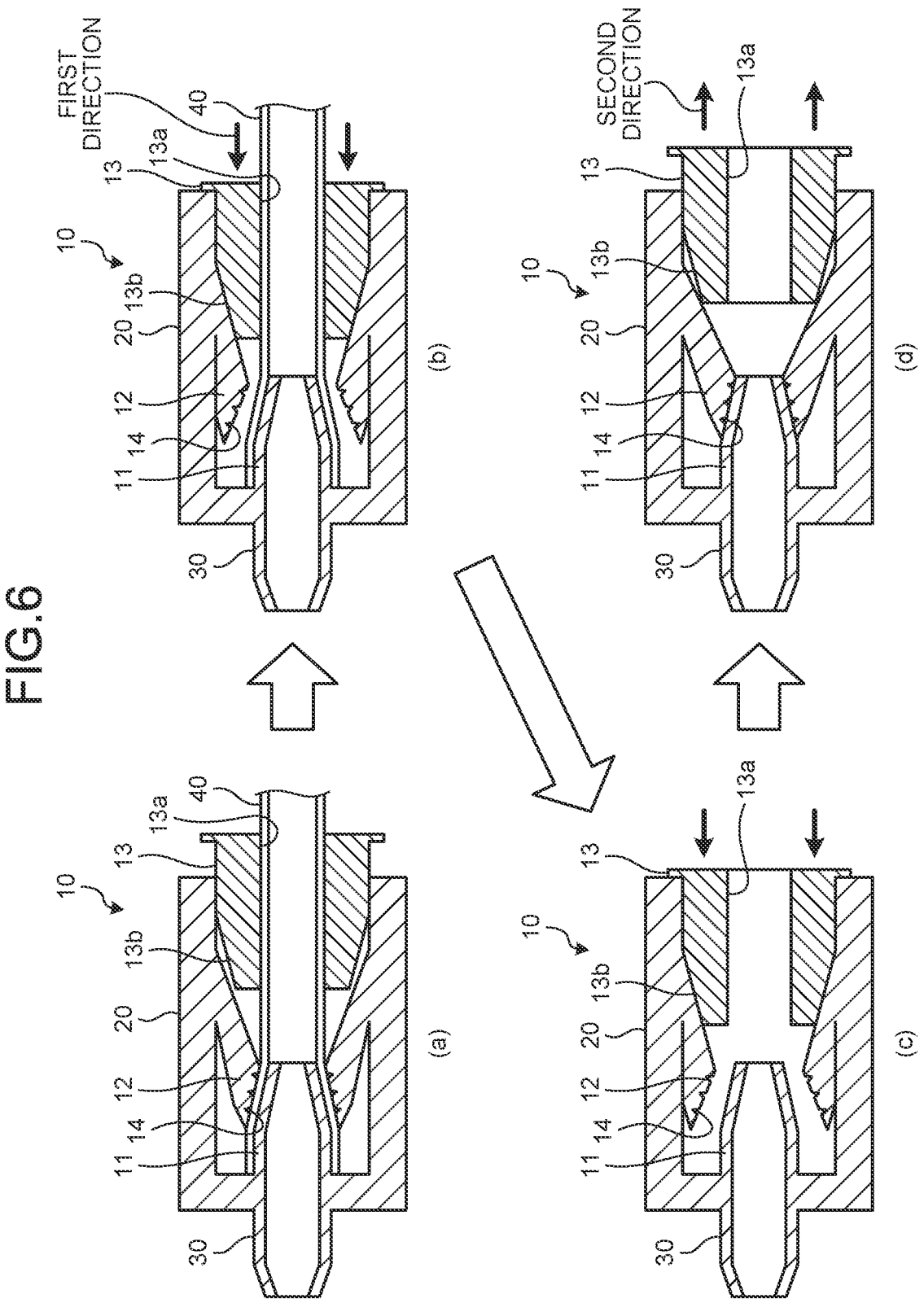
FIG. 6 is a diagram for explaining removal of the water supply tube from the connection joint.

Connection and removal between the water supply tube 40 and the connection joint 10 will be described below with reference to the drawings. FIG. 5 is a diagram for explaining connection between the water supply tube 40 and the connection joint 10, and FIG. 6 is a diagram for explaining removal of the water supply tube 40 from the connection joint 10.

First, in the state of the connection joint 10 as illustrated in (a) of FIG. 5, the bias releasing portion 13 is pressed in a first direction as illustrated in (b) of FIG. 5, so that the bias releasing portion 13 is pushed into the case main body 20. Consequently, the distal end portion 13b presses the pusher 12 to the outer peripheral side of the sleeve 11, and the bias applied by the pusher 12 to the sleeve 11 is released.

Subsequently, as illustrated in (c) of FIG. 5, the water supply tube 40 is inserted in the through hole a of the bias releasing portion 13, and the end portion of the water supply tube 40 is fitted to the sleeve 11.

After the water supply tube 40 as fitted to the sleeve 11, as illustrated in (d) of FIG. 5, the bias releasing portion 13 is pulled out in a second direction from the inside of the case main body 20. Consequently, the pusher 12 biases the sleeve 11, to which the water supply tube 40 is fitted, from the outer peripheral side of the sleeve 11, so that the water supply tube 40 and the connection joint 10 are connected.

In contrast, the water supply tube 40 is removed by, in the state as illustrated in (a) of FIG. 6, pressing the bias releasing portion 13 in the first direction as illustrated in (b) of FIG. 6, pushing the bias releasing portion 13 into the case main body 20, and releasing the bias applied by the pusher 12 to the sleeve 11.

Subsequently, as illustrated in (c) of FIG. 6, the water supply tube 40 is pulled out of the through hole a of the bias releasing portion 13 and removes the water supply tube 40 from the sleeve 11. After the water supply tube 40 is pulled out, as illustrated in (d) of FIG. 6, the bias releasing portion 13 is pulled out in the second direction from the inside of the case main body 20.

In the first embodiment, the water supply tube 40 is fixed to the sleeve 11 by causing the pusher 12 including the plate springs to apply bias to, from the outer peripheral side, the water supply tube 40 that is fitted to the sleeve 11, and the bias releasing portion 13 releases the bias applied by the pusher 12, so that it is possible to simplify connection and removal operation of the water supply tube 40 and reduce an operation time.

In the first embodiment, the endoscope 1 that includes connection joint 10 for connecting the water supply tube 40 has been explained; however, a tube to be connected by the connection joint 10 is not limited to the water supply tube 40, and the connection joint 10 may be used as a connection joint for general tubes, such as a treatment tool path tube, an air supply path tube, a suction path tube, a balloon water supply path tube, and a balloon air supply path tube.

Figure 7:
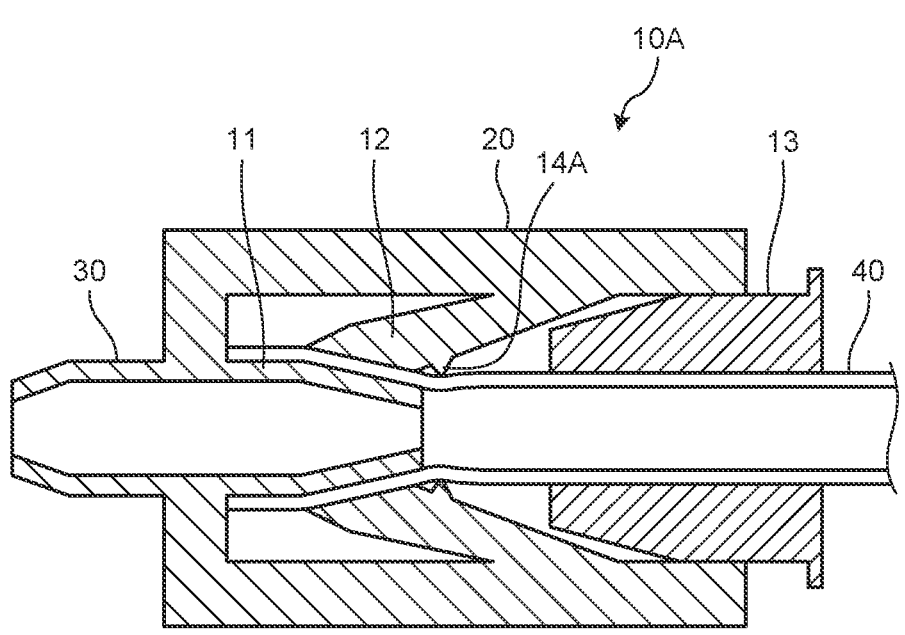
FIG. 7 is a cross-sectional view of a connection joint according to a first modification of the first embodiment of the disclosure.

Furthermore, in the first embodiment, the grooves 14 are formed, as the retainer, on the surface of the pusher 12 that comes into contact with the sleeve 11, but the retainer for preventing coming off of the water supply tube 40 is not limited to this example. FIG. 7 is a cross-sectional view of a connection joint 10A according to a first modification of the first embodiment of the disclosure in an axial direction. In the connection joint 10A, a protruding portion 14A is formed on the pusher 12 on a distal end side relative to the contact surface between the pusher 12 and the sleeve 11, and the protruding portion 14A presses the water supply tube 40 such that the protruding portion 14A that protrudes toward the tube 40 comes into contact with the water supply tube 40 and functions as a retainer that prevents coming off of the water supply tube 40.

Figure 8:
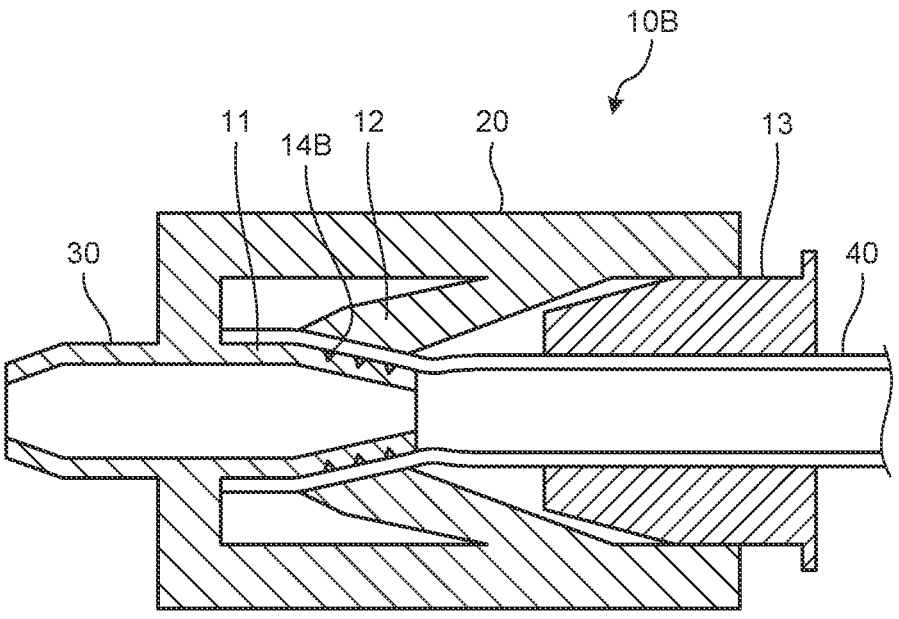
FIG. 8 is a cross-sectional view of a connection joint according to a second modification of the first embodiment of the disclosure.

Furthermore, the retainer may be formed on the sleeve 11. FIG. 8 is a cross-sectional view of a connection joint 10B according to a second modification of the first embodiment of the disclosure in an axial direction. In the connection joint 10B, grooves 14B that function as a retainer are arranged on a surface of the sleeve 11 that comes into contact with the pusher 12.

Second Embodiment

Figure 9:
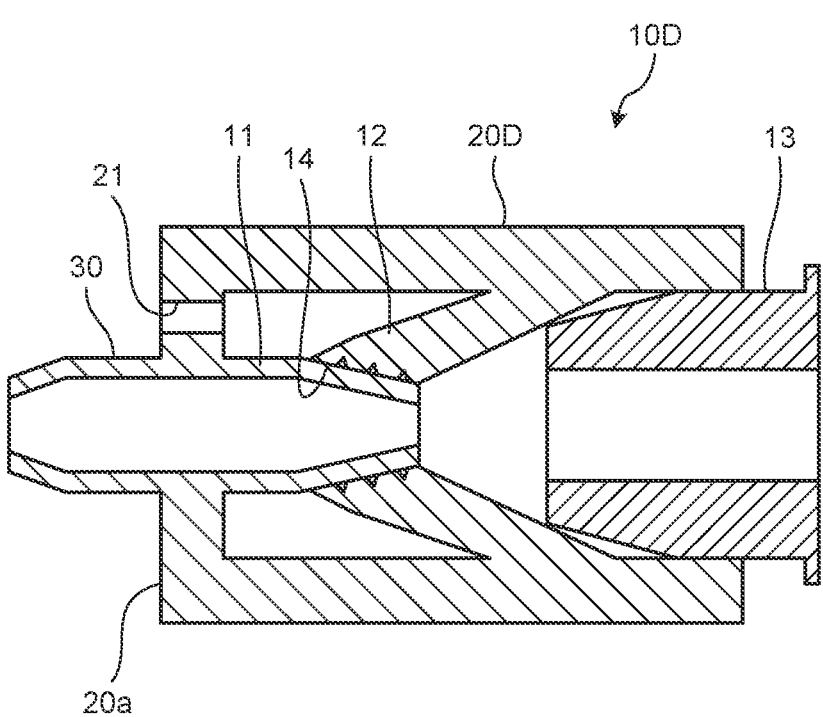
FIG. 9 is a cross-sectional view of a connection joint according to a second embodiment of the disclosure.

FIG. 9 is a cross-sectional view of a connection joint 10D according to a second embodiment of the disclosure in an axial direction. In the connection joint 10D, a case main body 20D includes a window portion 21 on an end portion that is not opened. In the connection joint 10 according to the first embodiment, the sleeve 11 is housed and held inside the case main body 20, so that it is not easy to check whether the water supply tube 40 is fitted to the sleeve 11; however, in the connection joint 10D, the window portion 21 is arranged on the bottomed surface 20a that is not opened in the case main body 20D in which the sleeve 11 is held, so that it is possible to check a fitting state of the water supply tube 40 with respect to the sleeve 11 from the window portion 21. Furthermore, the window portion 21 may be arranged on a side surface side if it is possible co observe the sleeve 11, in addition to the end portion that is not opened in the case main body 20D.

Meanwhile, it may be possible to form the case main body with transparent resin to implement a configuration that allows checking of the fitting state of the water supply tube 40 with respect to the sleeve 11, without arranging the window portion 21.

Third Embodiment

Figure 10:
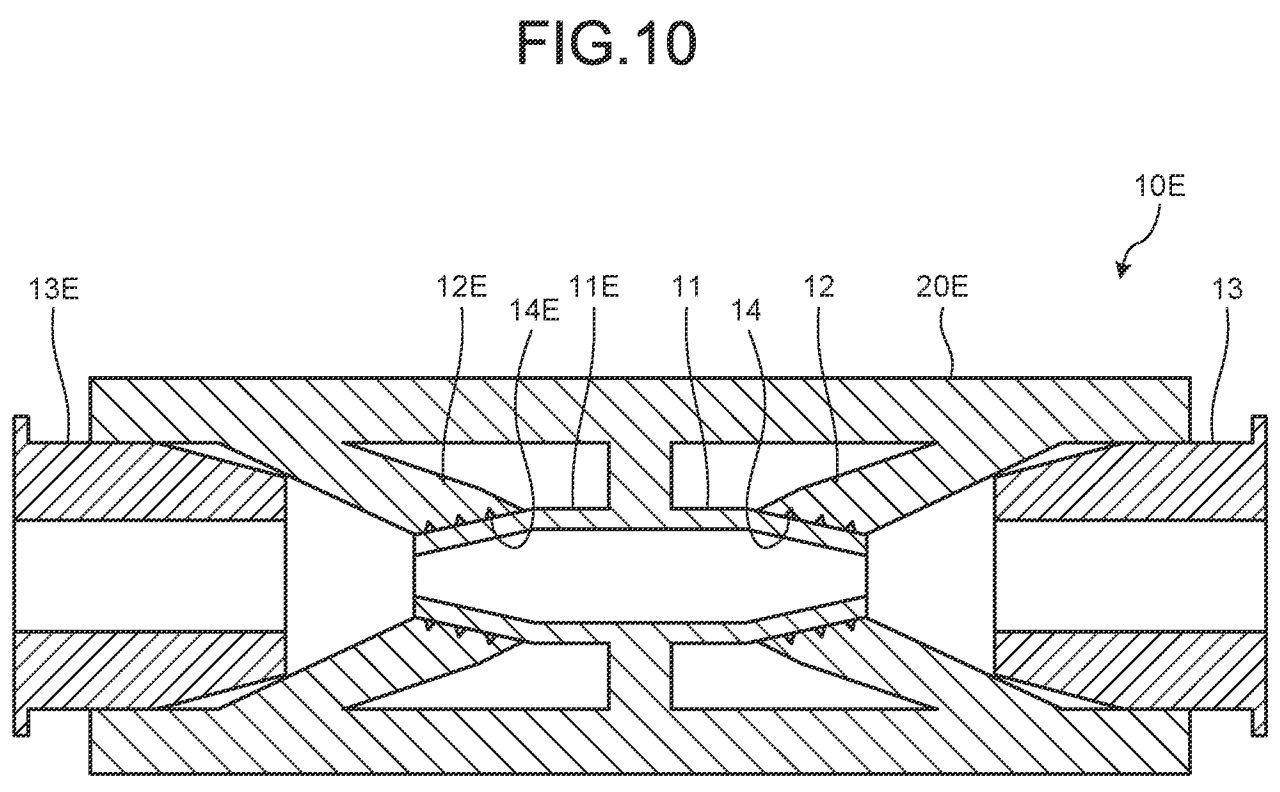

FIG. 10 is a cross-sectional view of a connection joint according to a third embodiment of the disclosure. A connection joint 10E includes, at a side opposite to the sleeve 11, a sleeve 11E, a pusher 12E, a bias releasing portion 13E, and grooves 14E, instead of the connection portion 30.

The connection joint 10E includes The sleeve 11 that is fitted to an end portion of a tube that constitutes a conduit path arranged inside the insertion portion 2 of the endoscope 1, the pusher 12 that applies bias to the sleeve 11 from an outer peripheral side of the sleeve 11, the bias releasing portion 13 that releases the bias by pressing, in an outer peripheral direction of the sleeve 11, the pusher 12 that is applying the bias to, from the outer peripheral side of the sleeve 11, the sleeve 11 to which the end portion of the tube is fitted. The connection joint 10E further includes the second sleeve 11E that is fitted to an end portion of a tube that constitutes a conduit path arranged at a side of the universal cord 4 of the endoscope 1, the second pusher 12E that applies bias to the second sleeve 11E from an outer peripheral side of the sleeve 11E, and the second bias releasing portion 13E that releases the bias by pressing, in an outer peripheral direction of the sleeve 11E, the second pusher 12E that is applying the bias to, from the cuter peripheral side of the sleeve 11E, the second sleeve 11E to which the end portion of the tube is fitted.

The grooves 14E are formed on a surface of the pusher 12E that comes into contact with the sleeve 11E, but it may be possible to arrange a protruding portion as the retainer instead of the grooves 14E, or it may be possible to arrange grooves on the sleeve 11E.

Fourth Embodiment

Figure 11:
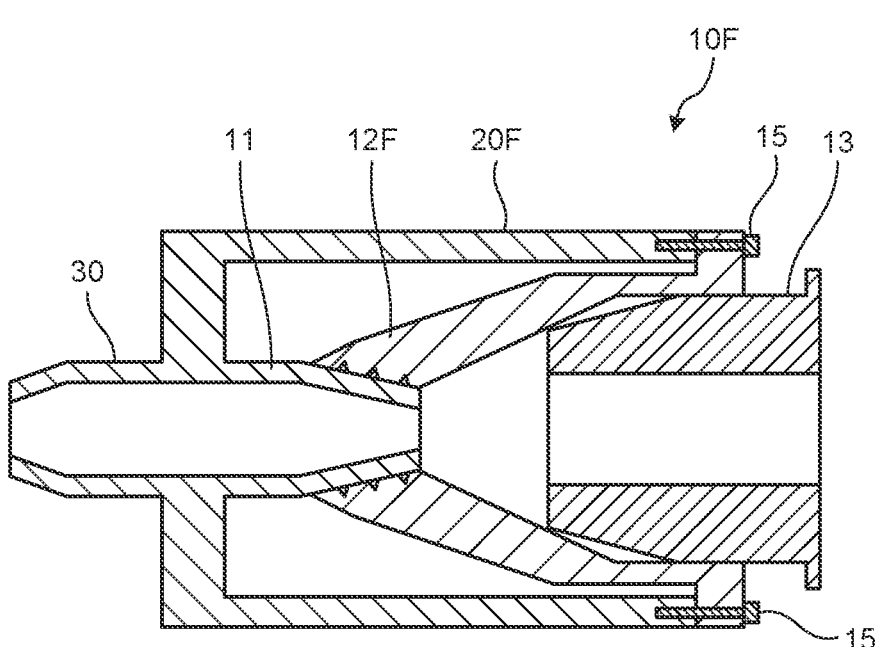
FIG. 11 is a cross-sectional view of a connection joint according to a fourth embodiment of the disclosure.

FIG. 11 is a cross-sectional view of a connection joint according to a fourth embodiment of the disclosure. In a connection joint 10F, a pusher 12F is separated from a case main body 20F. An end portion of the pusher 12F is fixed to an end portion of the case main body 20F by screws 15.

According to one aspect of the disclosure, it is possible to easily connect and remove a tube that constitutes a channel of an endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A connection joint comprising:
a case main body that has a tubular shape with a bottomed surface;
a first sleeve that is formed such that an end portion of a first tube arranged in an endoscope is externally fitted to the first sleeve, the first sleeve being integrally formed with the bottomed surface;
a first pusher having a first surface configured to directly apply a bias to the first tube from a first outer peripheral surface of the first sleeve; and a first bias releasing portion having a first bias releasing surface configured to press the first pusher in a direction toward the bottomed surface to release the bias;

wherein one of the first surface of the first pusher or the first outer peripheral surface of the first sleeve having a first retainer surface configured to prevent the first tube from coming off from the first sleeve; and the first retainer surface comprises first grooves that are aligned in a direction that is not parallel to a mounting direction of the first tube.

2. The connection joint according to claim 1, wherein the case main body being configured to internally hold the first sleeve, and the first pusher is fixed to an opening end portion of the case main body.

3. The connection joint according to claim 1, further comprising:

a second sleeve configured to be fitted to an end portion of a second tube comprising a conduit path arranged inside an insertion portion of the endoscope, the second sleeve being arranged on an opposite side of the first sleeve;

a second pusher having a second surface configured to directly apply a bias to the second sleeve from a second outer peripheral surface of the second sleeve; and a second bias releasing portion having a second bias releasing surface configured to press the second pusher, which is applying the bias to the second sleeve from the outer peripheral side of the second sleeve, in an outer peripheral direction of the second sleeve to release the bias of the second pusher, the end portion of the second tube being fitted to the second sleeve.

4. The connection joint according to claim 2, wherein the first pusher is integrated with the case main body.

5. The connection joint according to claim 2, wherein the case main body includes a window portion on the bottomed surface.

6. The connection joint according to claim 2, wherein the case main body is made of transparent resin.

7. The connection joint according to claim 3, wherein one of the second surface of the second pusher or a second outer peripheral surface of the second sleeve having a second retainer surface configured to prevent the second tube from coming off from the second sleeve.

8. The connection joint according to claim 7, wherein the second pusher having a second retainer surface comprising a protruding portion configured to be in contact with the second tube fitted to the second sleeve.

9. The connection joint according to claim 7, wherein the second pusher having a second pressed surface having a second retainer surface comprising a protruding portion, the second pressed surface being in contact with the second bias releasing surface, and the protruding portion is configured to be in contact with the second tube.

10. The connection joint according to claim 7, wherein the second retainer surface comprises second grooves that are aligned in a direction that is not parallel to a mounting direction of the second tube.

11. An endoscope comprising:

the connection joint according to claim 1.

12. A method of connecting a tube to a connection joint, the tube constituting a conduit path arranged inside an insertion portion of an endoscope, the method comprising:

releasing bias by pressing a pusher surface, which directly applies the bias to a sleeve integrally formed with a bottomed surface of the connection joint, from an outer peripheral surface of the sleeve, in an outer peripheral direction of the sleeve by pushing a bias releasing surface towards the bottomed surface;

fitting an end portion of the tube to the sleeve for which contact with the pusher surface is being released;

releasing pressing of the pusher surface by moving the bias releasing surface in a first direction such that the pusher surface moves in a direction away from the outer peripheral surface of the sleeve; and pressing the pusher surface toward the outer peripheral surface of the sleeve by moving the bias releasing surface in a second direction, different from the first direction.

13. The method according to claim 12, wherein the connection joint includes a retainer surface configured to be in contact with the tube by moving the bias releasing portion in the first direction.

14. A method of connecting a tube and a connection joint, the tube being arranged in an endoscope, the method comprising:

pressing a pusher surface, which directly applies bias to a sleeve integrally formed with a bottomed surface of the connection joint, to an outer peripheral surface of the sleeve, toward the bottomed surface to separate the sleeve from the pusher;

fitting the tube to the sleeve externally;

releasing pressing to the pusher surface; and applying, by the pusher surface, bias to an outer peripheral surface of the tube.

15. A connection joint comprising:

a case main body that has a tubular shape with a bottomed surface;

a first sleeve that is formed such that an end portion of a first tube arranged in an endoscope is externally fitted to the first sleeve, the first sleeve being integrally formed with the bottomed surface;

a first pusher having a first surface configured to directly apply a bias to the first tube from a first outer peripheral surface of the first sleeve; and a first bias releasing portion having a first bias releasing surface configured to press the first pusher in a direction toward the bottomed surface to release the bias;

wherein the first pusher includes a plurality of plate springs each having the first surface.

* * * * *